United States Patent [19]
Gazzara et al.

[11] Patent Number: 5,303,423
[45] Date of Patent: * Apr. 19, 1994

[54] FACE SHIELD/MASK COMBINATION

[75] Inventors: Peter J. Gazzara, Reading; John W. Burke, Jr., Melrose, both of Mass.

[73] Assignee: Splash Shield, Limited Partnership, Woburn, Mass.

[*] Notice: The portion of the term of this patent subsequent to May 19, 2009 has been disclaimed.

[21] Appl. No.: 712,065

[22] Filed: Jun. 7, 1991

Related U.S. Application Data

[63] Continuation-in-part of Ser. No. 464,297, Jan. 12, 1990, Pat. No. 5,113,528.

[51] Int. Cl.⁵ .......................... A42B 1/06; A61F 9/04
[52] U.S. Cl. .................................. 2/9; 2/181.8; 2/424; 128/857
[58] Field of Search ............... 2/9, 15, 410, 424, 431, 2/433, 181.8, DIG. 11; 128/857, 858, 863

[56] References Cited

U.S. PATENT DOCUMENTS

| | | | |
|---|---|---|---|
| 3,664,335 | 5/1972 | Boucher et al. | 128/863 |
| 4,825,878 | 5/1989 | Kuntz et al. | 2/9 |
| 4,852,185 | 8/1989 | Olson | 2/9 |
| 4,872,465 | 10/1989 | Kuntz et al. | 2/9 |
| 4,910,804 | 3/1990 | Lidgren | 2/181.8 |
| 4,944,312 | 7/1990 | Smith | 2/9 |
| 4,945,574 | 8/1990 | Dagher | 2/9 |
| 4,964,171 | 10/1990 | Landis | 2/9 |
| 4,965,887 | 10/1990 | Paoluccio et al. | 2/9 |
| 5,020,533 | 6/1991 | Hubbard et al. | 2/9 |
| 5,067,174 | 11/1991 | Ritchey et al. | 2/9 |
| 5,113,528 | 5/1992 | Burke, Jr. et al. | 2/9 |

FOREIGN PATENT DOCUMENTS 10106 11/1989 PCT Int'l Appl. .

Primary Examiner—William A. Cuchlinski, Jr.
Assistant Examiner—C. W. Fulton
Attorney, Agent, or Firm—Choate, Hall & Stewart

[57] ABSTRACT

Face shield for protecting a wearer's face from spatters. The shield includes a flexible, transparent portion sized to cover the face and a flexible spacer portion for contact with the wearer's forehead to provide adequate clearance of the transparent flexible portion away from the wearer's face. When worn, the flexible spacer portion substantially completely seals the top portion of the shield to prevent spatters from reaching the face from the top, that is, through the portion occupied by the spacer. The face shield may also include a mask structure to cover the nose and mouth of the wearer.

6 Claims, 3 Drawing Sheets

FACE SHIELD/MASK COMBINATION

This is a continuation-in-part of U.S. patent application Ser No. 07/464,297 filed Jan. 12, 1990, now U.S. Pat. No. 5,113,528 issued May 19, 1992.

BACKGROUND OF THE INVENTION

This invention relates to a shield to protect the face, especially from spattered fluids.

Liquids often spatter and come in contact with the face. While painting a ceiling, for example, a painter often finds that his face is flecked with spattered paint. During medical procedures, medical personnel are often subject to blood and other bodily fluids coming into contact with the face. Such contact is dangerous because of the potential presence of the deadly AIDS virus or other harmful pathogens.

FIG. 1 is a prior art face shield distributed by the Safe-T-Face Corporation of Beverly Hills, California. With reference to FIG. 1, a prior art disposable face shield 10 includes a transparent member 12 affixed to a cardboard framework 14 which folds flat for shipment and which expands to the configuration shown in FIG. 1 when worn by a person whose face is to be protected. The shield 10 is secured to a wearer (not shown) by an elastic band 16. Importantly, when worn the cardboard framework 14, which supports the transparent member 12 away from the face, creates a large gap 18 between a wearer's forehead and the front of the transparent member 12. Thus, spatters can travel through the wide gap 18 and land on the wearer's face. That is to say, the prior art face shield 10 will afford protection only from fluid spatters approaching the face from the front. On the other hand, spatters approaching the top of the head will readily pass through the gap 18 and land on the wearer's face.

SUMMARY OF THE INVENTION

The face shield according to the present invention includes a flexible, fluid impervious, transparent member sized to cover a human face. A flexible barrier and spacer member is affixed to a top portion of the transparent member and apparatus is provided for securing the transparent member/spacer member combination to the human face with the spacer member in contact with the forehead of the face. The barrier and spacer member creates a barrier between the forehead and the transparent member so as to prevent fluids approaching the head from the top from reaching the face.

In a preferred embodiment, the spacer member includes scallops proximate the forehead to facilitate comformance of the spacer with the forehead when worn. The spacer member is preferably pervious to air for the comfort of the wearer, but substantially impervious to liquid spatters. In this embodiment, the securing apparatus includes an elastic band. This band may be affixed to the transparent member or to the spacer member. It is preferred that the transparent member be made of a thin flexible plastic material and it is preferred that the spacer member be foam plastic.

In another embodiment of the invention, the face shield includes a mask structure affixed to the transparent member by affixing bands. The mask structure may be secured to the face shield wearer by loops or straps to cover the wearer's nose and mouth. Accordingly, the mask structure covers the nose and mouth of the face while the transparent member covers the entire human face.

Because the face shield of the invention employs a barrier and spacer member, spatters approaching the top of the head are prevented from contacting the wearer's face. This is unlike the known prior art device which affords no protection for spatters approaching the head from this direction.

DESCRIPTION OF THE PREFERRED EMBODIMENT

Figure 1:
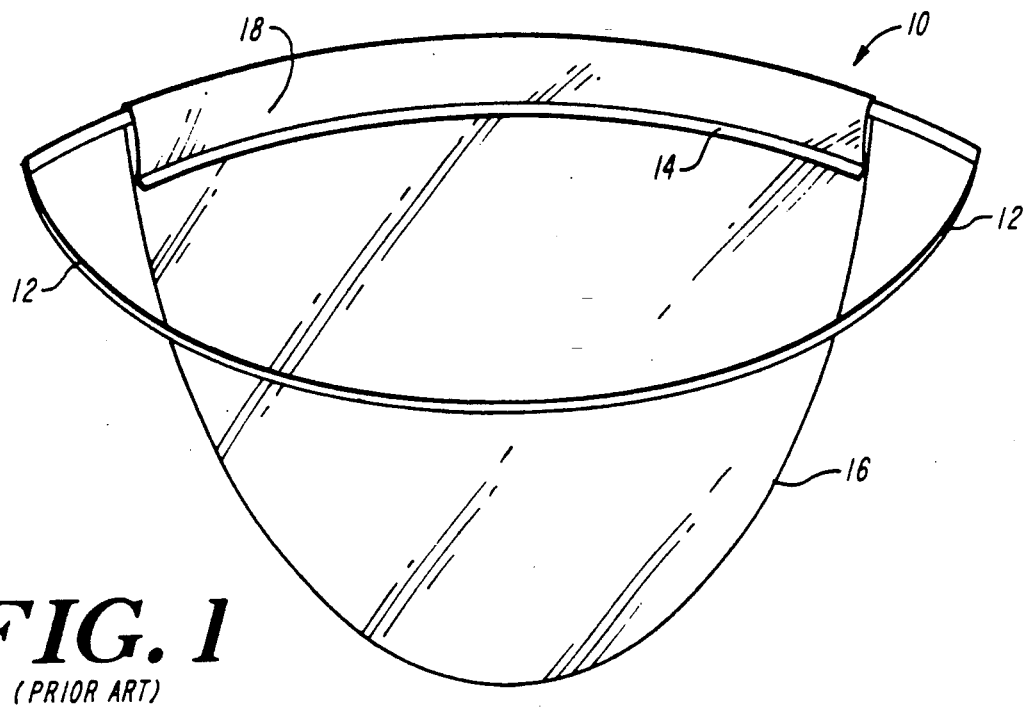
FIG. 1 is a perspective view of a prior art face shield.
Figure 2:
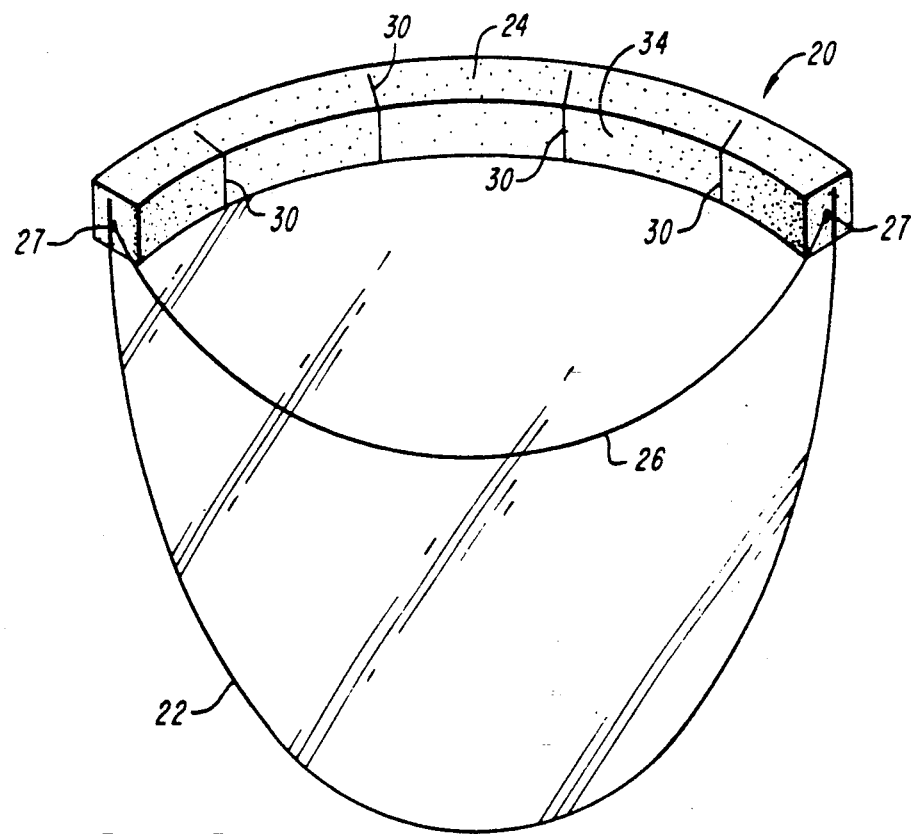
FIG. 2 is a perspective view of the face shield of the present invention.

With reference now to FIG. 2, a face shield 20 according to the invention includes a flexible, fluid impervious, transparent member 22 sized generally to cover a human face. Affixed to the top portion of the transparent member 22 by a suitable adhesive is a barrier and spacer member 24 which serves to space the transparent member 22 away from the face when the shield is being worn so that the transparent member 22 does not rest, for example, against the nose which would result in discomfort to the wearer. As will be described in detail hereinbelow, the spacer member 24 also serves as a barrier to the passage of fluids. An elastic band 26 is affixed either to the transparent member 22 or the spacer member 24 and serves to support the face shield 20 on the wearer's head with the spacer member 24 in contact with the wearer's forehead. It is advantageous that the elastic band 26 be attached at a location 27 below a center line of the spacer member 24 so that the shield 20 is urged toward the face when worn.

Figure 3:
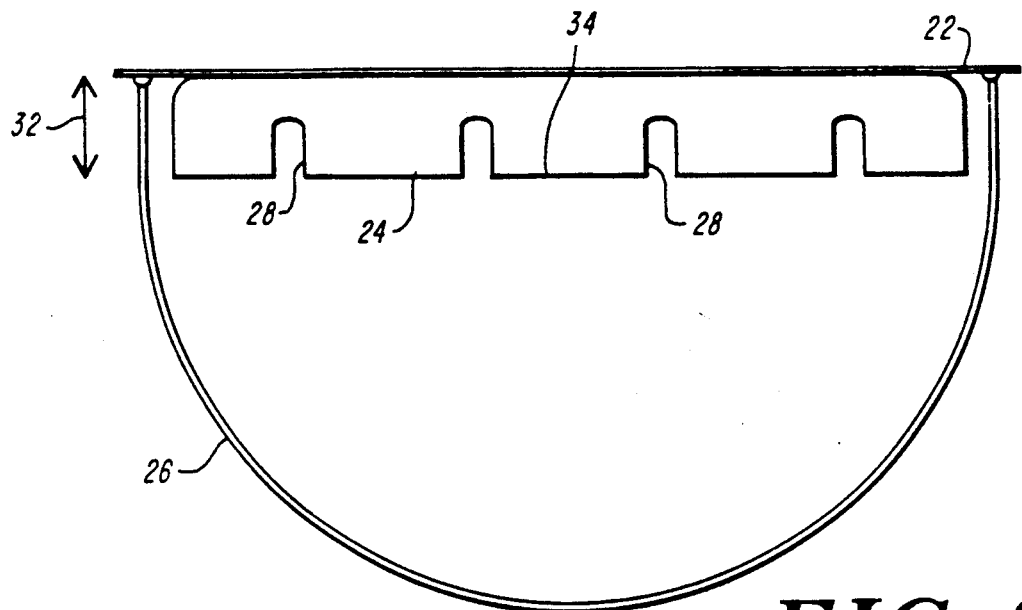
FIG. 3 is a top view of the shield of the invention.

As shown in FIG. 3, it is preferred that the spacer member 24 have a series of scallops 28 to facilitate bending to conform with a face shield wearer's forehead. The scallops can be die cut into the foam plastic. The scallops close completely when the face shield is worn, as shown by the lines 30 in FIG. 2, to serve as an effective barrier. An appropriate spacer dimension shown by an arrow 32 in FIG. 3 is approximately 1 ¾ inches.

Figure 4:
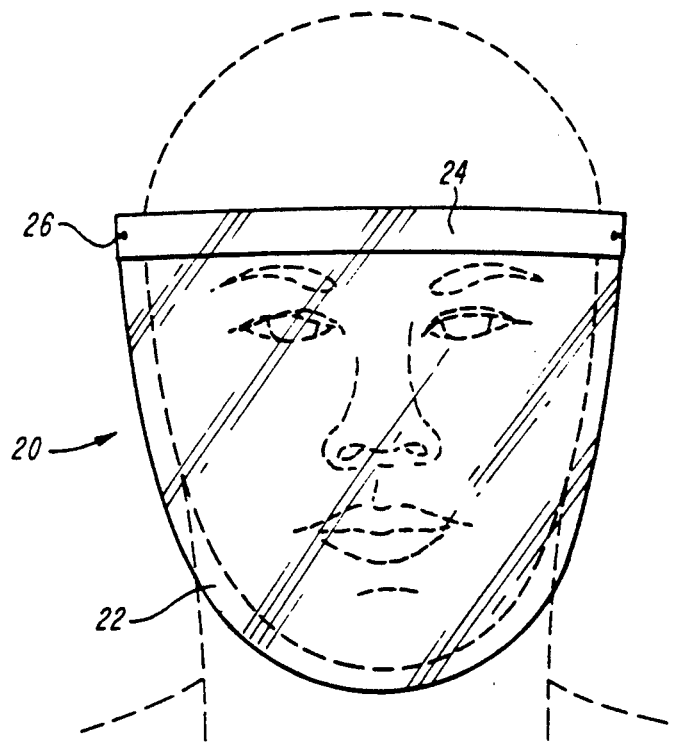
FIG. 4 is a front view of the shield of the invention shown placed on the head of a face shield wearer.

As shown in FIG. 4, the face shield 20 is worn with the spacer member 24 in contact with a wearer's forehead. The elastic band 26 encircles the head to hold the shield in place. When in place on the head, the spacer member 24 bends to conform with the curvature of the forehead and the scallops 28 completely close so that a solid barrier is provided to prevent fluids approaching from the top of the head direction from intersecting the face of a wearer. It is preferred that the spacer member 24 be made of a material, such as foam plastic, which allows the passage of air but which is substantially impervious to the passage of liquid spatters. The passage of air through the spacer member 24 reduces any tendency for fogging of the transparent member 22. In addition, small holes (not shown) can be made in the spacer member 24 to enhance air flow, but the holes should have a small size and angle so as not to permit spatters to pass through.

It is preferred that the transparent member 22 be made of polyester having a thickness of no less than five mils. A suitable material is available from Transilwrap Corporation of Elmwood, N.J. It is also preferred that the barrier and spacer member 24 be a foam plastic material such as white polyether having a 1.2 pound density. Those skilled in the art will readily appreciate that other materials may be utilized.

Figure 5:
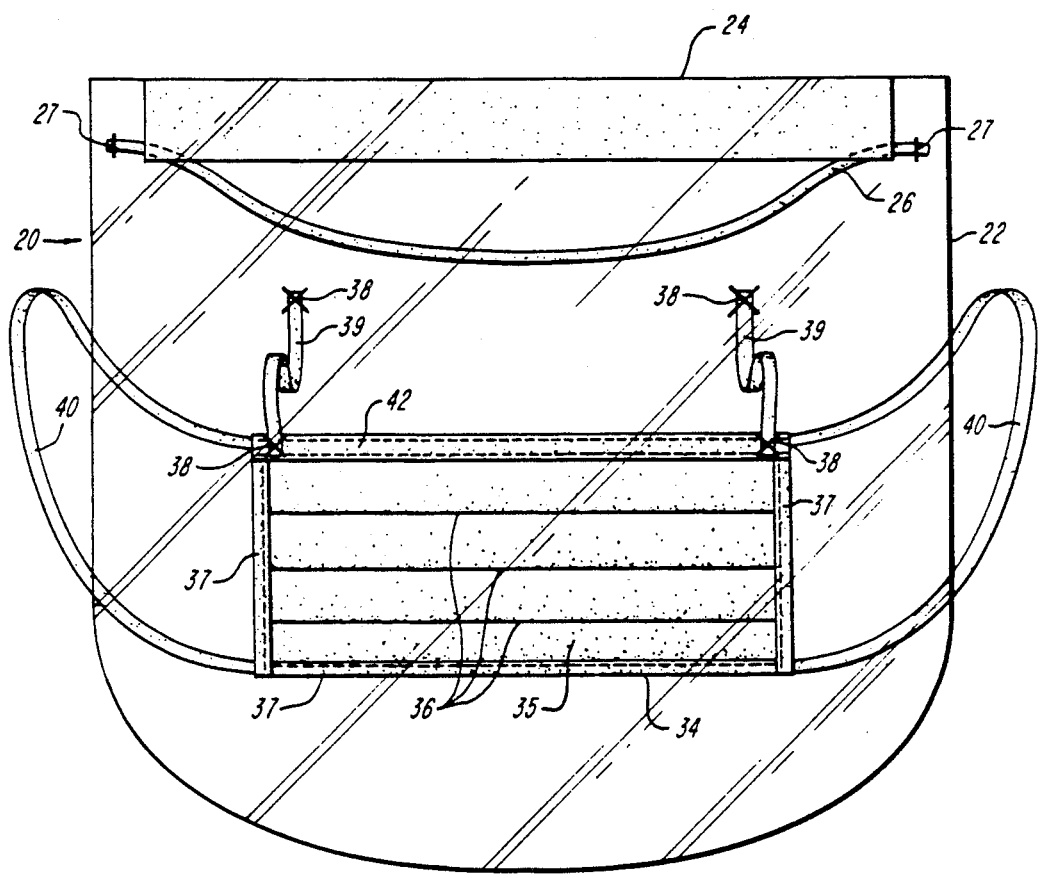
FIG. 5 is a front view of another embodiment of the invention.

Another embodiment of the invention is shown in FIG. 5. The face shield of this embodiment is substantially the same as that of FIGS. 2, 3, and 4, but includes a mask structure 34 having a lightweight fibrous material 35 which is air permeable, but substantially impervious to the passage of pathogens. The fibrous material 35 includes folds 36 secured by borders 37 surrounding the fibrous material 35. The borders 37 may be made of cloth material. As shown in FIG. 5, loops 40, connected to the mask structure 34, attach to the wearer's ears to secure the mask structure 34 to the wearer. Alternatively, straps (not shown) may replace loops 40 and secure the mask structure to the face by tying the straps behind the wearer's head. The mask structure 34 may also include a wire band 42 which bends to conform to the wearer's facial features allowing for a more comfortable mask structure 34 fitting.

The mask structure 34 in FIG. 5 further includes two bands 39 which attach the mask structure 34 to the transparent member 22 of the face shield 20. The bands 39 are secured to the mask structure 34 and to the transparent member 22 at points 38 by affixing means such as adhesives, welding, or sewing. The bands 39 may be of variable length and secured to either side of the mask structure 34 and/or to either side of the transparent member 22. The face shield/mask structure combination is secured to the wearer by first attaching the face shield 20 to the forehead of the wearer so that the transparent member 22 entirely covers the human face, then securing the mask structure 34 to the wearer so that the mask structure 34 covers the wearer's nose and mouth.

What is claimed is:

1. Face shield comprising:
    a flexible, fluid impervious, transparent member sized to cover a human face;
    a flexible barrier and spacer member affixed to a top portion of the transparent member, the barrier and spacer member substantially spanning the full extent of the transparent member and including
    a foam plastic material,
    a forehead engaging surface,
    a plurality of scallops extending into the barrier and spacer member from the forehead engaging surface;
    a mask structure affixed to the transparent member so that the nose and mouth of the human face is covered by the mask structure when secured to the human face; and
    apparatus for securing the transparent member/barrier and spacer member combination to the human face so that the forehead engaging surface of the barrier and spacer member contacts the forehead of the face,
    whereby when the transparent member/barrier and spacer combination is secured to the face, the scallops close so that the barrier and spacer member creates an air pervious and a substantially liquid impervious barrier between the forehead and the transparent member.

2. The face shield of claim 1 wherein
the mask structure includes an air permeable material.

3. The face shield of claim 1 wherein
the mask structure includes means for securing said mask structure to the human face.

4. The face shield of claim 1 wherein
the mask structure includes at least one wire band secured to the mask structure to allow the mask structure to conform to the features of the human face.

5. The face shield of claim 9 wherein
the mask structure is affixed to the transparent member by at least one affixing band.

6. Face shield comprising:
    a flexible, fluid impervious, transparent member sized to cover entirely a human face;
    a flexible barrier and spacer member affixed to a top portion of the transparent member, the barrier and spacer member spanning the full extent of the transparent member;
    a mask structure affixed to the transparent member to cover the nose and mouth of the human face, the mask structure having an air permeable material, means for securing said mask structure to the human face, a wire band secured to the mask structure to allow the mask structure to conform to the features of the human face, and at least one affixing band for affixing the mask structure to the transparent member; and
    apparatus for securing the transparent member/spacer member combination to the human face with the spacer member in contact with the forehead of the face, whereby the spacer member creates a barrier between the forehead and the transparent member.

* * * * *

UNITED STATES PATENT AND TRADEMARK OFFICE
CERTIFICATE OF CORRECTION

PATENT NO. : 5,303,423
DATED      : April 19, 1994
INVENTOR(S) : Peter J. Gazzara, et. al.

It is certified that error appears in the above-indentified patent and that said Letters Patent is hereby corrected as shown below:

Column 4, line 26, delete "9" and insert therefor --1 --.

Signed and Sealed this

First Day of November, 1994

Attest:

Attesting Officer

BRUCE LEHMAN

Commissioner of Patents and Trademarks